(12) United States Patent
Klyce et al.

(10) Patent No.: US 8,043,337 B2
(45) Date of Patent: Oct. 25, 2011

(54) IMPLANT SYSTEM AND METHOD TO TREAT DEGENERATIVE DISORDERS OF THE SPINE

(75) Inventors: Henry A. Klyce, Piedmont, CA (US); James F. Zucherman, San Francisco, CA (US); Ken Y. Hsu, San Francisco, CA (US); Matthew Hannibal, San Francisco, CA (US)

(73) Assignee: Spartek Medical, Inc., Alameda, CA (US)

( * ) Notice: Subject to any disclaimer, the term of this patent is extended or adjusted under 35 U.S.C. 154(b) by 956 days.

(21) Appl. No.: 11/761,100

(22) Filed: Jun. 11, 2007

(65) Prior Publication Data

US 2008/0058807 A1 Mar. 6, 2008

Related U.S. Application Data

(60) Provisional application No. 60/801,871, filed on Jun. 14, 2006.

(51) Int. Cl.
*A61B 17/70* (2006.01)
(52) U.S. Cl. ........................................................ 606/252
(58) Field of Classification Search ................. 606/60, 606/246, 250, 254, 257, 276, 252
See application file for complete search history.

(56) References Cited

U.S. PATENT DOCUMENTS

| | | | |
|---|---|---|---|
| 4,041,939 A | 8/1977 | Hall | 128/69 |
| 4,065,817 A | 1/1978 | Branemark et al. | 3/1.91 |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |

(Continued)

FOREIGN PATENT DOCUMENTS

DE 2649042 B1 10/1976

(Continued)

OTHER PUBLICATIONS

"Functional Lumbar Artificial Nucleus Replacement: The DASCOR System," J.E. Sherman et al., *Dynamic Reconstruction of the Spine*, Section III, Restoration of Lumbar Motion Segment, A. Lumbar Nucleus Replacement, Chapter 15, 2006, pp. 114-121.

(Continued)

*Primary Examiner* — Thomas C. Barrett
*Assistant Examiner* — Sameh Boles
(74) *Attorney, Agent, or Firm* — Fliesler Meyer LLP

(57) ABSTRACT

A spinal implant system includes at each spinal level a flexible horizontal rod to which are mounted two opposing clamps. The clamps wrap around the facets of a vertebra to secure the horizontal rod to the vertebra. A stiff vertical connector system connects the flexible horizontal rod secured at one level of the spine to a flexible horizontal rod secured at an adjacent level of the spine. The vertical connector system is spaced along the flexible horizontal rod away from the opposing clamps. The flexible horizontal rods are preferably made of PEEK or Nitinol. The opposing clamps and vertical connector system are preferably made of titanium or stainless steel. Bending of the flexible horizontal rod permits movement of the opposing clamps relative to the vertical rod. The spinal implant system thereby provides for dynamic stabilization and motion preservation of the spine.

20 Claims, 6 Drawing Sheets

U.S. PATENT DOCUMENTS

| | | | | |
|---|---|---|---|---|
| 4,479,491 A | 10/1984 | Martin | | 128/92 |
| 4,567,885 A | 2/1986 | Androphy | | 128/92 |
| 4,573,454 A | 3/1986 | Hoffman | | 128/69 |
| 4,604,995 A | 8/1986 | Stephens et al. | | 128/69 |
| 4,611,580 A | 9/1986 | Wu | | 128/69 |
| 4,611,581 A | 9/1986 | Steffee | | 128/69 |
| 4,611,582 A | 9/1986 | Duff | | 128/69 |
| 4,641,636 A | 2/1987 | Cotrel | | 128/69 |
| 4,648,388 A | 3/1987 | Steffee | | 128/69 |
| 4,653,481 A | 3/1987 | Howland et al. | | 128/69 |
| 4,653,489 A | 3/1987 | Tronzo | | 128/92 |
| 4,655,199 A | 4/1987 | Steffee | | 128/69 |
| 4,658,809 A | 4/1987 | Ulrich et al. | | 128/92 |
| 4,696,290 A | 9/1987 | Steffee | | 128/69 |
| 4,719,905 A | 1/1988 | Steffee | | 128/69 |
| 4,763,644 A | 8/1988 | Webb | | 128/69 |
| 4,773,402 A | 9/1988 | Asher et al. | | 128/69 |
| 4,805,602 A | 2/1989 | Puno et al. | | 128/69 |
| 4,815,453 A | 3/1989 | Cotrel | | 128/69 |
| 4,887,595 A | 12/1989 | Heinig et al. | | 606/61 |
| 4,913,134 A | 4/1990 | Luque | | 128/69 |
| 4,946,458 A | 8/1990 | Harms et al. | | 606/61 |
| 4,950,269 A | 8/1990 | Gaines, Jr. | | 606/61 |
| 4,955,885 A | 9/1990 | Meyers | | 606/53 |
| 4,987,892 A | 1/1991 | Krag et al. | | 606/61 |
| 5,005,562 A | 4/1991 | Cotrel | | 128/69 |
| 5,024,213 A | 6/1991 | Asher et al. | | 128/69 |
| 5,030,220 A | 7/1991 | Howland | | 606/61 |
| 5,042,982 A | 8/1991 | Harms et al. | | 606/61 |
| 5,047,029 A | 9/1991 | Aebi et al. | | 606/61 |
| 5,067,955 A | 11/1991 | Cotrel | | 606/61 |
| 5,074,864 A | 12/1991 | Cozad et al. | | 606/54 |
| 5,084,049 A | 1/1992 | Asher et al. | | 606/61 |
| 5,092,866 A | 3/1992 | Breard et al. | | 606/61 |
| 5,102,412 A | 4/1992 | Rogozinski | | 606/61 |
| 5,112,332 A | 5/1992 | Cozad et al. | | 606/61 |
| 5,113,685 A | 5/1992 | Asher et al. | | 72/458 |
| 5,127,912 A | 7/1992 | Ray et al. | | 606/61 |
| 5,129,388 A | 7/1992 | Vignaud et al. | | 606/61 |
| 5,129,900 A | 7/1992 | Asher et al. | | 606/61 |
| 5,147,359 A | 9/1992 | Cozad et al. | | 606/61 |
| 5,154,718 A | 10/1992 | Cozad et al. | | 606/61 |
| 5,176,680 A | 1/1993 | Vignaud et al. | | 606/61 |
| 5,180,393 A | 1/1993 | Commarmond | | 623/13 |
| 5,190,543 A | 3/1993 | Schläpfer | | 606/61 |
| 5,201,734 A | 4/1993 | Cozad et al. | | 606/62 |
| 5,207,678 A | 5/1993 | Harms et al. | | 606/61 |
| 5,261,911 A | 11/1993 | Carl | | 606/61 |
| 5,261,912 A | 11/1993 | Frigg | | 606/61 |
| 5,261,913 A | 11/1993 | Marnay | | 606/61 |
| 5,281,222 A | 1/1994 | Allard et al. | | 606/54 |
| 5,282,801 A | 2/1994 | Sherman | | 606/61 |
| 5,282,863 A | 2/1994 | Burton | | 623/17 |
| 5,290,289 A | 3/1994 | Sanders et al. | | 606/61 |
| 5,312,402 A | 5/1994 | Schläpfer et al. | | 606/53 |
| 5,312,404 A | 5/1994 | Asher et al. | | 606/61 |
| 5,344,422 A | 9/1994 | Frigg | | 606/61 |
| 5,346,493 A | 9/1994 | Stahurski et al. | | 606/61 |
| 5,360,429 A | 11/1994 | Jeanson et al. | | 606/61 |
| 5,360,431 A | 11/1994 | Puno et al. | | 606/72 |
| 5,380,325 A | 1/1995 | Lahille et al. | | 606/61 |
| 5,380,326 A | 1/1995 | Lin | | 606/61 |
| 5,382,248 A | 1/1995 | Jacobson et al. | | 606/60 |
| 5,385,583 A | 1/1995 | Cotrel | | 623/17 |
| 5,387,213 A | 2/1995 | Breard et al. | | 606/61 |
| 5,403,316 A * | 4/1995 | Ashman | | 606/250 |
| 5,415,661 A | 5/1995 | Holmes | | 606/69 |
| 5,429,639 A | 7/1995 | Judet | | 606/61 |
| 5,443,467 A | 8/1995 | Biedermann et al. | | 606/65 |
| 5,466,237 A | 11/1995 | Byrd, III et al. | | 606/61 |
| 5,474,555 A | 12/1995 | Puno et al. | | 606/73 |
| 5,487,742 A | 1/1996 | Cotrel | | 606/61 |
| 5,496,321 A | 3/1996 | Puno et al. | | 606/61 |
| 5,498,264 A | 3/1996 | Schlapfer et al. | | 606/72 |
| 5,520,689 A | 5/1996 | Schläpfer et al. | | 606/61 |
| 5,534,001 A | 7/1996 | Schläpfer et al. | | 606/61 |
| 5,536,268 A | 7/1996 | Griss | | 606/61 |
| 5,540,688 A | 7/1996 | Navas | | 606/61 |
| 5,545,167 A | 8/1996 | Lin | | 606/61 |
| 5,549,607 A | 8/1996 | Olson et al. | | 606/61 |
| 5,562,737 A | 10/1996 | Graf | | 623/17 |
| 5,569,248 A | 10/1996 | Mathews | | 606/61 |
| 5,609,592 A | 3/1997 | Brumfield et al. | | 606/61 |
| 5,609,593 A | 3/1997 | Errico et al. | | 606/61 |
| 5,611,800 A | 3/1997 | Davis et al. | | 606/61 |
| 5,624,441 A | 4/1997 | Sherman et al. | | 606/61 |
| 5,628,740 A | 5/1997 | Mullane | | 606/61 |
| 5,630,816 A | 5/1997 | Kambin | | 606/61 |
| 5,643,260 A | 7/1997 | Doherty | | 606/61 |
| 5,645,599 A | 7/1997 | Samani | | 623/17 |
| 5,651,789 A | 7/1997 | Cotrel | | 606/61 |
| 5,653,708 A | 8/1997 | Howland | | 606/61 |
| 5,658,284 A | 8/1997 | Sebastian et al. | | 606/61 |
| 5,667,506 A | 9/1997 | Sutterlin | | 606/61 |
| 5,667,507 A | 9/1997 | Corin et al. | | 606/61 |
| 5,669,910 A | 9/1997 | Korhonen et al. | | 606/61 |
| 5,672,175 A | 9/1997 | Martin | | 606/61 |
| 5,672,176 A | 9/1997 | Biedermann et al. | | 606/61 |
| 5,676,665 A | 10/1997 | Bryan | | 606/61 |
| 5,676,703 A | 10/1997 | Gelbard | | 623/17 |
| 5,681,311 A | 10/1997 | Foley et al. | | 606/61 |
| 5,681,319 A | 10/1997 | Biedermann et al. | | 606/104 |
| 5,683,391 A | 11/1997 | Boyd | | 606/61 |
| 5,683,392 A | 11/1997 | Richelsoph et al. | | 606/61 |
| 5,683,393 A | 11/1997 | Ralph | | 606/61 |
| 5,688,272 A | 11/1997 | Montague et al. | | 606/61 |
| 5,688,273 A | 11/1997 | Errico et al. | | 606/61 |
| 5,690,629 A | 11/1997 | Asher et al. | | 606/61 |
| 5,690,632 A | 11/1997 | Schwartz et al. | | 606/73 |
| 5,690,633 A | 11/1997 | Taylor et al. | | 606/73 |
| 5,693,053 A | 12/1997 | Estes | | 606/61 |
| 5,697,929 A | 12/1997 | Mellinger | | 606/61 |
| 5,700,292 A | 12/1997 | Margulies | | 623/17 |
| 5,702,392 A | 12/1997 | Wu et al. | | 606/61 |
| 5,702,394 A | 12/1997 | Henry et al. | | 606/61 |
| 5,702,395 A | 12/1997 | Hopf | | 606/61 |
| 5,702,396 A | 12/1997 | Hoenig et al. | | 606/69 |
| 5,702,399 A | 12/1997 | Kilpela et al. | | 606/72 |
| 5,702,452 A | 12/1997 | Argenson et al. | | 623/17 |
| 5,713,900 A | 2/1998 | Benzel et al. | | 606/61 |
| 5,713,904 A | 2/1998 | Errico et al. | | 606/73 |
| 5,716,355 A | 2/1998 | Jackson et al. | | 606/61 |
| 5,716,356 A | 2/1998 | Biedermann et al. | | 606/61 |
| 5,716,357 A | 2/1998 | Rogozinski | | 606/61 |
| 5,716,358 A | 2/1998 | Ochoa et al. | | 606/62 |
| 5,716,359 A | 2/1998 | Ojima et al. | | 606/76 |
| 5,720,751 A | 2/1998 | Jackson | | 606/86 |
| 5,725,528 A | 3/1998 | Errico et al. | | 606/61 |
| 5,725,582 A | 3/1998 | Bevan et al. | | 623/17 |
| 5,728,098 A | 3/1998 | Sherman et al. | | 606/61 |
| 5,733,286 A | 3/1998 | Errico et al. | | 606/61 |
| 5,735,851 A | 4/1998 | Errico et al. | | 606/61 |
| 5,741,254 A | 4/1998 | Henry et al. | | 606/61 |
| 5,743,907 A | 4/1998 | Asher et al. | | 606/61 |
| 5,743,911 A | 4/1998 | Cotrel | | 606/61 |
| 5,752,957 A | 5/1998 | Ralph et al. | | 606/61 |
| 5,766,254 A | 6/1998 | Gelbard | | 623/17 |
| 5,776,135 A | 7/1998 | Errico et al. | | 606/61 |
| 5,782,833 A | 7/1998 | Haider | | 606/61 |
| 5,785,711 A | 7/1998 | Errico et al. | | 606/61 |
| 5,797,911 A | 8/1998 | Sherman et al. | | 606/61 |
| 5,800,435 A | 9/1998 | Errico et al. | | 606/61 |
| 5,810,819 A | 9/1998 | Errico et al. | | 606/61 |
| 5,863,293 A | 1/1999 | Richelsoph | | 606/61 |
| 5,879,350 A | 3/1999 | Sherman et al. | | 606/61 |
| 5,885,286 A | 3/1999 | Sherman et al. | | 606/61 |
| 5,891,145 A | 4/1999 | Morrison et al. | | 606/61 |
| 5,899,904 A | 5/1999 | Errico et al. | | 606/61 |
| RE36,221 E | 6/1999 | Breard et al. | | 606/61 |
| 5,910,142 A | 6/1999 | Tatar | | 606/61 |
| 5,925,047 A | 7/1999 | Errico et al. | | 606/65 |
| 5,928,231 A | 7/1999 | Klein et al. | | 606/60 |
| 5,928,232 A | 7/1999 | Howland et al. | | 606/61 |
| 5,928,233 A | 7/1999 | Apfelbaum et al. | | 606/61 |
| 5,947,965 A | 9/1999 | Bryan | | 606/61 |
| 5,947,969 A | 9/1999 | Errico et al. | | 606/61 |
| 5,954,725 A | 9/1999 | Sherman et al. | | 606/78 |

| Patent No. | Date | Inventor | Class |
|---|---|---|---|
| 5,961,517 A | 10/1999 | Biedermann et al. | 606/61 |
| 5,964,760 A | 10/1999 | Richelsoph | 606/61 |
| 5,980,521 A | 11/1999 | Montague et al. | 606/61 |
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,036,693 A | 3/2000 | Yuan et al. | 606/61 |
| 6,050,997 A | 4/2000 | Mullane | 606/61 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,273,888 B1 | 8/2001 | Justis | 606/61 |
| 6,273,914 B1 | 8/2001 | Papas | 623/17.11 |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schäffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,589,243 B1 * | 7/2003 | Viart et al. | 606/250 |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht | 128/898 |
| 6,887,242 B2 | 5/2005 | Doubler et al. | 606/61 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |
| 7,018,378 B2 | 3/2006 | Biedermann et al. | 606/61 |
| 7,018,379 B2 | 3/2006 | Drewry | 606/61 |
| 7,022,122 B2 | 4/2006 | Amrein et al. | 606/61 |
| 7,029,475 B2 | 4/2006 | Panjabi | 606/61 |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,214,227 B2 | 5/2007 | Colleran et al. | 606/61 |
| 7,250,052 B2 | 7/2007 | Landry et al. | 606/61 |
| 7,282,064 B2 | 10/2007 | Chin | 623/17.15 |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,326,210 B2 | 2/2008 | Jahng et al. | 606/61 |
| 7,335,201 B2 | 2/2008 | Doubler et al. | 606/61 |
| 7,763,051 B2 * | 7/2010 | Labrom et al. | 606/248 |

| | | | | | | |
|---|---|---|---|---|---|---|
| 2002/0013586 A1 | 1/2002 | Justis et al. | | 2005/0240180 A1 | 10/2005 | Vienney et al. |
| 2002/0026192 A1 | 2/2002 | Schmiel et al. | | 2005/0240265 A1 | 10/2005 | Kuiper et al. |
| 2002/0068975 A1 | 6/2002 | Teitelbaum et al. | | 2005/0240266 A1 | 10/2005 | Kuiper et al. |
| 2002/0082603 A1 | 6/2002 | Dixon et al. | | 2005/0261770 A1 | 11/2005 | Kuiper et al. |
| 2002/0120271 A1 | 8/2002 | Dixon et al. | | 2005/0267470 A1 | 12/2005 | McBride |
| 2002/0143329 A1 | 10/2002 | Serhan et al. | | 2005/0267472 A1 | 12/2005 | Biedermann et al. |
| 2002/0169450 A1 | 11/2002 | Lange | | 2005/0277922 A1 | 12/2005 | Trieu et al. |
| 2003/0004511 A1 | 1/2003 | Ferree | | 2005/0277925 A1 | 12/2005 | Mujwid |
| 2003/0073996 A1 | 4/2003 | Doubler et al. | | 2005/0277927 A1 | 12/2005 | Guenther et al. |
| 2003/0073997 A1 | 4/2003 | Doubler et al. | | 2005/0277928 A1 | 12/2005 | Boschert |
| 2003/0083657 A1 | 5/2003 | Drewry et al. | | 2005/0288670 A1 | 12/2005 | Panjabi et al. |
| 2003/0125742 A1 | 7/2003 | Yuan et al. | | 2005/0288671 A1 | 12/2005 | Yuan et al. |
| 2003/0171749 A1 | 9/2003 | Le Couedic et al. | | 2006/0004357 A1 | 1/2006 | Lee et al. |
| 2004/0015166 A1 | 1/2004 | Gorek | | 2006/0025771 A1 | 2/2006 | Jackson |
| 2004/0030337 A1 | 2/2004 | Alleyne et al. | | 2006/0030839 A1 | 2/2006 | Park et al. |
| 2004/0039384 A1 | 2/2004 | Boehm, Jr. et al. | | 2006/0036240 A1* | 2/2006 | Colleran et al. ............... 606/61 |
| 2004/0097925 A1 | 5/2004 | Boehm, Jr. et al. | | 2006/0036242 A1 | 2/2006 | Nilsson et al. |
| 2004/0097933 A1 | 5/2004 | Lourdel et al. | | 2006/0036324 A1 | 2/2006 | Sachs et al. |
| 2004/0111088 A1 | 6/2004 | Picetti et al. | | 2006/0052783 A1 | 3/2006 | Dant et al. |
| 2004/0116929 A1 | 6/2004 | Barker et al. | | 2006/0052784 A1 | 3/2006 | Dant et al. |
| 2004/0122425 A1 | 6/2004 | Suzuki et al. | | 2006/0052786 A1 | 3/2006 | Dant et al. |
| 2004/0138662 A1 | 7/2004 | Landry et al. | | 2006/0058787 A1 | 3/2006 | David |
| 2004/0143264 A1 | 7/2004 | McAfee | | 2006/0058788 A1 | 3/2006 | Hammer et al. |
| 2004/0143265 A1 | 7/2004 | Landry et al. | | 2006/0058790 A1 | 3/2006 | Carl et al. |
| 2004/0147928 A1 | 7/2004 | Landry et al. | | 2006/0064090 A1 | 3/2006 | Park |
| 2004/0153077 A1 | 8/2004 | Biedermann et al. | | 2006/0064091 A1 | 3/2006 | Ludwig et al. |
| 2004/0158245 A1 | 8/2004 | Chin | | 2006/0069391 A1 | 3/2006 | Jackson |
| 2004/0158247 A1 | 8/2004 | Sitiso et al. | | 2006/0074419 A1 | 4/2006 | Taylor et al. |
| 2004/0162560 A1 | 8/2004 | Raynor et al. | | 2006/0079894 A1 | 4/2006 | Colleran et al. |
| 2004/0172022 A1 | 9/2004 | Landry et al. | | 2006/0079896 A1 | 4/2006 | Kwak et al. |
| 2004/0172024 A1 | 9/2004 | Gorek | | 2006/0084978 A1 | 4/2006 | Mokhtar |
| 2004/0215192 A1 | 10/2004 | Justis et al. | | 2006/0084980 A1 | 4/2006 | Melkent et al. |
| 2004/0225289 A1 | 11/2004 | Biedermann et al. | | 2006/0084982 A1 | 4/2006 | Kim |
| 2004/0230192 A1 | 11/2004 | Graf | | 2006/0084983 A1 | 4/2006 | Kim |
| 2004/0236327 A1 | 11/2004 | Paul et al. | | 2006/0084984 A1 | 4/2006 | Kim |
| 2004/0236330 A1 | 11/2004 | Purcell et al. | | 2006/0084985 A1 | 4/2006 | Kim |
| 2005/0033441 A1 | 2/2005 | Lambrecht et al. | | 2006/0084987 A1 | 4/2006 | Kim |
| 2005/0049589 A1 | 3/2005 | Jackson | | 2006/0084988 A1 | 4/2006 | Kim |
| 2005/0065515 A1 | 3/2005 | Jahng | | 2006/0084989 A1 | 4/2006 | Dickinson et al. |
| 2005/0070899 A1 | 3/2005 | Doubler et al. | | 2006/0084990 A1 | 4/2006 | Gournay et al. |
| 2005/0070901 A1 | 3/2005 | David | | 2006/0084993 A1 | 4/2006 | Landry et al. |
| 2005/0080415 A1 | 4/2005 | Keyer et al. | | 2006/0084995 A1 | 4/2006 | Biedermann et al. |
| 2005/0085813 A1 | 4/2005 | Spitler et al. | | 2006/0085069 A1 | 4/2006 | Kim |
| 2005/0090822 A1 | 4/2005 | DiPoto | | 2006/0085070 A1 | 4/2006 | Kim |
| 2005/0096652 A1 | 5/2005 | Burton | | 2006/0089643 A1 | 4/2006 | Mujwid |
| 2005/0096659 A1 | 5/2005 | Freudiger | | 2006/0089644 A1 | 4/2006 | Felix |
| 2005/0107788 A1 | 5/2005 | Beaurain et al. | | 2006/0095035 A1 | 5/2006 | Jones et al. |
| 2005/0113927 A1 | 5/2005 | Malek | | 2006/0095038 A1 | 5/2006 | Jackson |
| 2005/0113929 A1 | 5/2005 | Cragg et al. | | 2006/0100621 A1 | 5/2006 | Jackson |
| 2005/0119658 A1 | 6/2005 | Ralph et al. | | 2006/0100622 A1 | 5/2006 | Jackson |
| 2005/0124991 A1 | 6/2005 | Jahng | | 2006/0106380 A1 | 5/2006 | Colleran et al. |
| 2005/0131404 A1 | 6/2005 | Mazda et al. | | 2006/0106383 A1 | 5/2006 | Biedermann et al. |
| 2005/0131405 A1 | 6/2005 | Molz, IV et al. | | 2006/0111712 A1 | 5/2006 | Jackson |
| 2005/0131406 A1 | 6/2005 | Reiley et al. | | 2006/0111715 A1 | 5/2006 | Jackson |
| 2005/0143737 A1 | 6/2005 | Pafford et al. | | 2006/0116676 A1 | 6/2006 | Gradel et al. |
| 2005/0143823 A1 | 6/2005 | Boyd et al. | | 2006/0122597 A1 | 6/2006 | Jones et al. |
| 2005/0171537 A1 | 8/2005 | Mazel et al. | | 2006/0122599 A1 | 6/2006 | Drewry et al. |
| 2005/0171543 A1 | 8/2005 | Timm et al. | | 2006/0122620 A1 | 6/2006 | Kim |
| 2005/0177156 A1 | 8/2005 | Timm et al. | | 2006/0129147 A1 | 6/2006 | Biedermann et al. |
| 2005/0177157 A1 | 8/2005 | Jahng | | 2006/0129148 A1 | 6/2006 | Simmons et al. |
| 2005/0177164 A1 | 8/2005 | Walters et al. | | 2006/0129149 A1 | 6/2006 | Iott et al. |
| 2005/0177166 A1 | 8/2005 | Timm et al. | | 2006/0142761 A1 | 6/2006 | Landry et al. |
| 2005/0182400 A1 | 8/2005 | White | | 2006/0149231 A1 | 7/2006 | Bray |
| 2005/0182401 A1 | 8/2005 | Timm et al. | | 2006/0149232 A1 | 7/2006 | Sasing |
| 2005/0182409 A1 | 8/2005 | Callahan et al. | | 2006/0149234 A1 | 7/2006 | de Coninck |
| 2005/0187548 A1 | 8/2005 | Butler et al. | | 2006/0149237 A1 | 7/2006 | Markworth et al. |
| 2005/0192569 A1 | 9/2005 | Nichols et al. | | 2006/0149238 A1 | 7/2006 | Sherman et al. |
| 2005/0192571 A1 | 9/2005 | Abdelgany | | 2006/0149240 A1 | 7/2006 | Jackson |
| 2005/0192572 A1 | 9/2005 | Abdelgany et al. | | 2006/0149242 A1 | 7/2006 | Kraus et al. |
| 2005/0203514 A1 | 9/2005 | Jahng et al. | | 2006/0149244 A1 | 7/2006 | Amrein et al. |
| 2005/0203517 A1 | 9/2005 | Jahng et al. | | 2006/0149380 A1 | 7/2006 | Lotz et al. |
| 2005/0203518 A1 | 9/2005 | Biedermann et al. | | 2006/0155277 A1 | 7/2006 | Metz-Stavenhagen |
| 2005/0222570 A1 | 10/2005 | Jackson | | 2006/0155278 A1 | 7/2006 | Warnick |
| 2005/0228375 A1 | 10/2005 | Mazda et al. | | 2006/0161153 A1 | 7/2006 | Hawkes et al. |
| 2005/0228382 A1 | 10/2005 | Richelsoph et al. | | 2006/0173456 A1 | 8/2006 | Hawkes et al. |
| 2005/0228385 A1 | 10/2005 | Iott et al. | | 2006/0189983 A1 | 8/2006 | Fallin et al. |
| 2005/0234451 A1 | 10/2005 | Markworth | | 2006/0195093 A1 | 8/2006 | Jahng |
| 2005/0234454 A1 | 10/2005 | Chin | | 2006/0200128 A1 | 9/2006 | Mueller |
| 2005/0234557 A1 | 10/2005 | Lambrecht et al. | | 2006/0200130 A1 | 9/2006 | Hawkins et al. |

| | | |
|---|---|---|
| 2006/0200131 A1 | 9/2006 | Chao et al. |
| 2006/0200133 A1 | 9/2006 | Jackson |
| 2006/0217716 A1 | 9/2006 | Baker et al. |
| 2006/0229606 A1 | 10/2006 | Clement et al. |
| 2006/0229607 A1 | 10/2006 | Brumfield |
| 2006/0229613 A1 | 10/2006 | Timm et al. |
| 2006/0229615 A1 | 10/2006 | Abdou |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241594 A1 | 10/2006 | McCarthy et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 * | 10/2006 | Trautwein et al. ............ 606/61 |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247624 A1 | 11/2006 | Bonouskou et al. |
| 2006/0247628 A1 | 11/2006 | Rawlins et al. |
| 2006/0247631 A1 | 11/2006 | Ahn et al. |
| 2006/0247636 A1 | 11/2006 | Yuan et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0005062 A1 | 1/2007 | Lange et al. |
| 2007/0005063 A1 | 1/2007 | Bruneau et al. |
| 2007/0016190 A1 | 1/2007 | Martinez et al. |
| 2007/0016201 A1 | 1/2007 | Freudiger |
| 2007/0032123 A1 | 2/2007 | Timm et al. |
| 2007/0043356 A1 | 2/2007 | Timm et al. |
| 2007/0043358 A1 | 2/2007 | Molz, VI et al. |
| 2007/0049936 A1 | 3/2007 | Colleran et al. |
| 2007/0073289 A1 | 3/2007 | Kwak et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0093829 A1 | 4/2007 | Abdou |
| 2007/0118122 A1 | 5/2007 | Butler et al. |
| 2007/0123861 A1 | 5/2007 | Dewey et al. |
| 2007/0123871 A1 | 5/2007 | Jahng |
| 2007/0156143 A1 | 7/2007 | Lancial |
| 2007/0161994 A1 | 7/2007 | Lowery et al. |
| 2007/0161997 A1 | 7/2007 | Thramann et al. |
| 2007/0162007 A1 | 7/2007 | Shoham |
| 2007/0167947 A1 | 7/2007 | Gittings |
| 2007/0168035 A1 | 7/2007 | Koske |
| 2007/0198014 A1 | 8/2007 | Graf et al. |
| 2007/0213714 A1 | 9/2007 | Justis |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233075 A1 | 10/2007 | Dawson |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0244481 A1 | 10/2007 | Timm |
| 2007/0250061 A1 | 10/2007 | Chin et al. |
| 2007/0270819 A1 | 11/2007 | Justis et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021285 A1 | 1/2008 | Drzyzga et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0045951 A1 | 2/2008 | Fanger et al. |
| 2008/0045957 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |

FOREIGN PATENT DOCUMENTS

| | | |
|---|---|---|
| DE | 3639810 A1 | 5/1988 |
| EP | 0128058 A1 | 12/1984 |
| EP | 0669109 B1 | 8/1995 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2880256 B1 | 7/2006 |
| GB | 780652 | 8/1957 |
| GB | 2173104 | 10/1986 |
| GB | 2382304 | 5/2003 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO 2004/024011 | 3/2004 |
| WO | WO 2004/034916 | 4/2004 |
| WO | WO 2006/033503 | 3/2006 |
| WO | WO 2006/066685 | 6/2006 |
| WO | WO 2006/105935 | 10/2006 |
| WO | WO 2007/080317 | 7/2007 |
| WO | WO 2008/034130 | 3/2008 |

OTHER PUBLICATIONS

"NeuDisc," R. Bertagnoli et al., *Dynamic Reconstruction of the Spine*, Section III, Restoration of Lumbar Motion Segment, A. Lumbar Nucleus Replacement, Chapter 16, 2006, pp. 122-126.

"Pioneer Surgical Technology NUBAC Artificial Nucleus," Q. Bao et al., *Dynamic Reconstruction of the Spine*, Section III, Restoration of Lumbar Motion Segment, A. Lumbar Nucleus Replacement, Chapter 17, 2006, pp. 128-136.

"SINUX (Sinitec)," J. Zoellner, *Dynamic Reconstruction of the Spine*, Section III, Restoration of Lumbar Motion Segment, A. Lumbar Nucleus Replacement, Chapter 18, 2006, pp. 137-141.

"Nucore Injectable Disk Nucleus," S.H. Kitchel et al., *Dynamic Reconstruction of the Spine*, Section III, Restoration of Lumbar Motion Segment, A. Lumbar Nucleus Replacement, Chapter 19, 2006, pp. 142-146.

"Biomechanical Considerations for Total Lumbar Disk Replacement," J. LeHuec et al., *Dynamic Reconstruction of the Spine*, Section III, Restoration of Lumbar Motion Segment, B. Lumbar Total Disk Replacement, Chapter 20, 2006, pp. 149-153.

"Indications for Total Lumbar Disk Replacement," R. Bertagnoli, *Dynamic Reconstruction of the Spine*, Section III, Restoration of Lumbar Motion Segment, B. Lumbar Total Disk Replacement, Chapter 21, 2006, pp. 154-159.

"Charté Artificial Disc," F.H. Geisler, *Dynamic Reconstruction of the Spine*, Section III, Restoration of Lumbar Motion Segment, B. Lumbar Total Disk Replacement, Chapter 22, 2006, pp. 160-178.

"ProDisc Lumbar Artificial Disk," J.E.Zigler et al., *Dynamic Reconstruction of the Spine*, Section III, Restoration of Lumbar Motion Segment, B. Lumbar Total Disk Replacement, Chapter 23, 2006, pp. 179-185.

"MAVERICK Total Disc Replacement," M.F.Gornet, *Dynamic Reconstruction of the Spine*, Section III, Restoration of Lumbar Motion Segment, B. Lumbar Total Disk Replacement, Chapter 24, 2006, pp. 186-195.

"The Mobidisc Prosthesis," J.P. Steib et al., *Dynamic Reconstruction of the Spine*, Section III, Restoration of Lumbar Motion Segment, B. Lumbar Total Disk Replacement, Chapter 25, 2006, pp. 196-203.

"Activ-L Lumbar (Aesculap) Total Disk Arthroplasty," J.J. Yue et al., *Dynamic Reconstruction of the Spine*, Section III, Restoration of Lumbar Motion Segment, B. Lumbar Total Disk Replacement, Chapter 26, 2006, pp. 204-211.

"The FlexiCore Disk," A.D. Sharan et al., *Dynamic Reconstruction of the Spine*, Section III, Restoration of Lumbar Motion Segment, B. Lumbar Total Disk Replacement, Chapter 27, 2006, pp. 212-220.

"Management of Vascular and Surgical Approach—Related Complications for Lumbar Total Disk Replacement," S.H. Lee et al., *Dynamic Reconstruction of the Spine*, Section III, Restoration of Lumbar Motion Segment, B. Lumbar Total Disk Replacement, Chapter 28, 2006, pp. 221-226.

"Complications of Lumbar Disk Arthroplasty," SH Lee et al., *Dynamic Reconstruction of the Spine*, Section III, Restoration of Lumbar Motion Segment, B. Lumbar Total Disk Replacement, Chapter 29, 2006, pp. 227-233.

"Rationale for Dynamic Stabilization," D.S. McNally, *Dynamic Reconstruction of the Spine*, Section III, Restoration of Lumbar Motion Segment, C. Dynamic Posterior Stabilization, Chapter 30, 2006, pp. 237-243.

"Rationale for Dynamic Stabilization II—SoftFlex System," D.K. Sengupta, *Dynamic Reconstruction of the Spine*, Section III, Restoration of Lumbar Motion Segment, C. Dynamic Posterior Stabilization, Chapter 31, 2006, pp. 244-250.

"The X STOP Interspinous Process Decompression System for the Treatment of Lumbar Neurogenic Claudication," R.M. Thunder et al., *Dynamic Reconstruction of the Spine*, Section III, Restoration of Lumbar Motion Segment, C. Dynamic Posterior Stabilization, Chapter 32, 2006, pp. 251-257.

"Dynamic Lumbar Stabilization with the Wallis Interspinous Implant," J. Sénégas, *Dynamic Reconstruction of the Spine*, Section III, Restoration of Lumbar Motion Segment, C. Dynamic Posterior Stabilization, Chapter 33, 2006, pp. 258-267.

"Coflex," ES Kim et al., *Dynamic Reconstruction of the Spine*, Section III, Restoration of Lumbar Motion Segment, C. Dynamic Posterior Stabilization, Chapter 34, 2006, pp. 268-273.

DIAM (Device for Intervertebral Assisted Motion) Spinal Stabilization System, K. Singh et al., *Dynamic Reconstruction of the Spine*, Section III, Restoration of Lumbar Motion Segment, C. Dynamic Posterior Stabilization, Chapter 35, 2006, pp. 274-283.

"Tension Band System," SH Lee et al., *Dynamic Reconstruction of the Spine*, Section III, Restoration of Lumbar Motion Segment, C. Dynamic Posterior Stabilization, Chapter 36, 2006, pp. 284-291.

"Shape Memory Implant (KIMPF-DI Fixing) System," YS Kim et al., *Dynamic Reconstruction of the Spine*, Section III, Restoration of Lumbar Motion Segment, C. Dynamic Posterior Stabilization, Chapter 37, 2006, pp. 292-298.

"Treatment of Mobile Vertebral Instability with Dynesys," G. Dubois et al., *Dynamic Reconstruction of the Spine*, Section III, Restoration of Lumbar Motion Segment, C. Dynamic Posterior Stabilization, Chapter 38, 2006, pp. 299-304.

"Graf Soft Stabilization: Graf Ligamentoplasty," YS Kim et al., *Dynamic Reconstruction of the Spine*, Section III, Restoration of Lumbar Motion Segment, C. Dynamic Posterior Stabilization, Chapter 39, 2006, pp. 305-311.

"Isobar TTL Dynamic Instrumentation," A.E. Castellvi et al., *Dynamic Reconstruction of the Spine*, Section III, Restoration of Lumbar Motion Segment, C. Dynamic Posterior Stabilization, Chapter 40, 2006, pp. 312-322.

"Minimally Invasive Posterior Dynamic Stabilization System," L. Pimenta et al., *Dynamic Reconstruction of the Spine*, Section III Restoration of Lumbar Motion Segment, C. Dynamic Posterior Stabilization, Chapter 41, 2006, pp. 323-329.

"Nonfusion Stabilization of the Degenerated Lumbar Spine with Cosmic," A. von Strempel, *Dynamic Reconstruction of the Spine*, Section III, Retoration of Lumbar Motion Segment, C. Dynamic Posterior Stabilization, Chapter 42, 2006, pp. 330-339.

"BioFlex Spring Rod Pedicle Screw System," YS Kim et al., *Dynamic Reconstruction of the Spine*, Section III, Restoration of Lumbar Motion Segment, C. Dynamic Posterior Stabilization, Chapter 43, 2006, pp. 340-344.

"Facet Replacement Technologies," M.R. Lim et al., *Dynamic Reconstruction of the Spine*, Section III, Restoration of Lumbar Motion Segment, D. Facet Replacement, Chapter 44, 2006, pp. 347-353.

"TOPS—Total Posterior Facet Replacement and Dynamic Motion Segment Stabilization System," L.T. Khoo et al., *Dynamic Reconstruction of the Spine*, Section III, Restoration of Lumbar Motion Segment, D. Facet Replacement, Chapter 45, 2006, pp. 354-363.

"Total Facet Arthroplasty System (TFAS)," S. Webb, *Dynamic Reconstruction of the Spine*, Section III, Restoration of Lumbar Motion Segment, D. Facet Replacement, Chapter 46, 2006, pp. 364-371.

"Indications and Techniques in Annuloplasty," M.Y. Wang, *Dynamic Reconstruction of the Spine*, Section III, Restoration of Lumbar Motion Segment, E. Annular Repair, Chapter 47, 2006, pp. 375-379.

"Molecular Therapy of the Intervertebral Disk," S.T. Yoon, *Dynamic Reconstruction of the Spine*, Section IV, Future Biological Approaches to Disk Repair, Chapter 48, 2006, pp. 383-388.

*Dynamic Reconstruction of the Spine*, D.H. Kim et al., 2006, Index, pp. 389-402.

International Search Report for PCT/US07/70981 dated Apr. 23, 2008, 7 pages.

"Biomechanical Testing Protocol for Evaluating Cervical Disk Arthroplasty," D.J. DiAngelo et al., *Dynamic Reconstruction of the Spine*, Section II, Restoration of Cervical Motion Segment, Chapter 4, 2006, pp. 33-41.

"Cervical Disk Arthroplasty: Rationale, Indications, and Clinical Experience," M.R. Lim et al., *Dynamic Reconstruction of the Spine*, Section II, Restoration of Cervical Motion Segment, Chapter 5, 2006, pp. 42-51.

"Spinal Kinetics Cervical Disc," D.H. Kim et al., *Dynamic Reconstruction of the Spine*, Section II, Restoration of Cervical Motion Segment, Chapter 6, 2006, pp. 52-58.

"Bryan Cervical Disc Device," R. Hacker, *Dynamic Reconstruction of the Spine*, Section II, Restoration of Cervical Motion Segment, Chapter 7, 2006, pp. 59-66.

"Prestige Cervical Artificial Disk," J.T. Robertson, *Dynamic Reconstruction of the Spine*, Section II, Restoration of Cervical Motion Segment, Chapter 8, 2006, pp. 67-71.

"ProDisc-C Cervical Artificial Disk" G.K. Jeong et al., *Dynamic Reconstruction of the Spine*, Section II, Restoration of Cervical Motion Segment, Chapter 9, 2006, pp. 72-77.

"PCM (Porous Coated Motion) Artificial Cervical Disc," L Pimenta et al., *Dynamic Reconstruction of the Spine*, Section II, Restoration of Cervical Motion Segment, Chapter 10, 2006, pp. 78-85.

"Cervidisc Concept: Six-Year Follow-Up and Introducing Cervidisc II: DISCOVERV," A.S. Ramadan et al., *Dynamic Reconstruction of the Spine*, Section II, Restoration of Cervical Motion Segment, Chapter 11, 2006, pp. 86-91.

"CerviCore Cervical Intervertebral Disk Replacement," S.S. Lee et al., *Dynamic Reconstruction of the Spine*, Section II, Restoration of Cervical Motion Segment, Chapter 12, 2006, pp. 92-95.

"Prosthetic Disk Nucleus Partial Disk Replacement: Pathobiological and Biomechanical Rationale for Design and Function," C.D. Ray et al., *Dynamic Reconstruction of the Spine*, Section III, Restoration of Lumbar Motion Segment, A. Lumbar Nucleus Replacement, Chapter 13, 2006, pp. 99-104.

"The Raymedica Prosthetic Disk Nucleus (PDN): Stabilizing the Degenerated Lumbar Vertebral Segment without Fusion or Total Disk Replacement," C.D. Ray, *Dynamic Reconstruction of the Spine*, Section III, Restoration of Lumbar Motion Segment, A. Lumbar Nucleus Replacement, Chapter 14, pp. 105-113.

International Search Report for PCT/US/08/65435 dated Sep. 2, 2008, 4 pages.

International Search Report for PCT/US/08/65434 dated Oct. 9, 2008, 4 pages.
Mekanika—The Spinal Stabilization Company, product description for Modulus System, 2 pages, http://mekanika.com/htm/modsystem.htm.
Zimmer Spine, product description for Dynesis—The Dynamic Stabilization System, 5 pages, http://www.zimmer.com/ctl?template=IN&action=1&op=global&id=9165&pr=Y.
ITOIKA Medical Instruments, product description for S-Plate, 15 pages, http://ito-ika.co.jp/s-plate/splate1.pdf and http://ito-ika.co.jp/s-plate/splate1.pdf.
"Flexible rods and the case for dynamic stabilization," Jason M. Highsmith, M.D., et al., *Neurosurg. Focus*, vol. 22, Jan. 2007, pp. 1-5.
"The Spinous Process: The Forgotten Appendage," Kenneth R. Kattan, M. D. eta 1., *Skeletal Radiology*, vol. 6, 1981, pp. 199-204.
"Morphological and functional changes of the lumbar spinous processes in the elderly," R. Scapinelli, *Surgical Radiologic Anatomy*, vol. 11, 1989, pp. 129-133.

"The Paraspinal Sacrospinalis-Splitting Approach to the Lumbar Spine," Leon L. Wiltse et al., *The Journal of Bone & Joint Surgery*, vol. 50-A, No. 5, Jul. 1968 pp. 919-926.
*Dynamic Reconstruction of the Spine*, D.H. Kim et al., 2006, cover through p. xix.
"Historical Review of Spinal Arthroplasty and Dynamic Stabilizations," K M. Shibata et al., *Dynamic Reconstruction of the Spine*, Section I, Motion Preservation of the Spine, Chapter 1, 2006, pp. 3-15.
"Current Concepts in Spinal Fusion versus Nonfusion," D.H. Walker et al., *Dynamic Reconstruction of the Spine*, Section I, Motion Preservation of the Spine, Chapter 2, 2006, pp. 16-23.
"Biomechanical Aspects Associated with Cervical Disk Arthroplasty," D.J. DiAngelo et al., *Dynamic Reconstruction of the Spine*, Section II, Restoration of Cervical Motion Segment, Chapter 3, 2006, pp. 27-32.

* cited by examiner

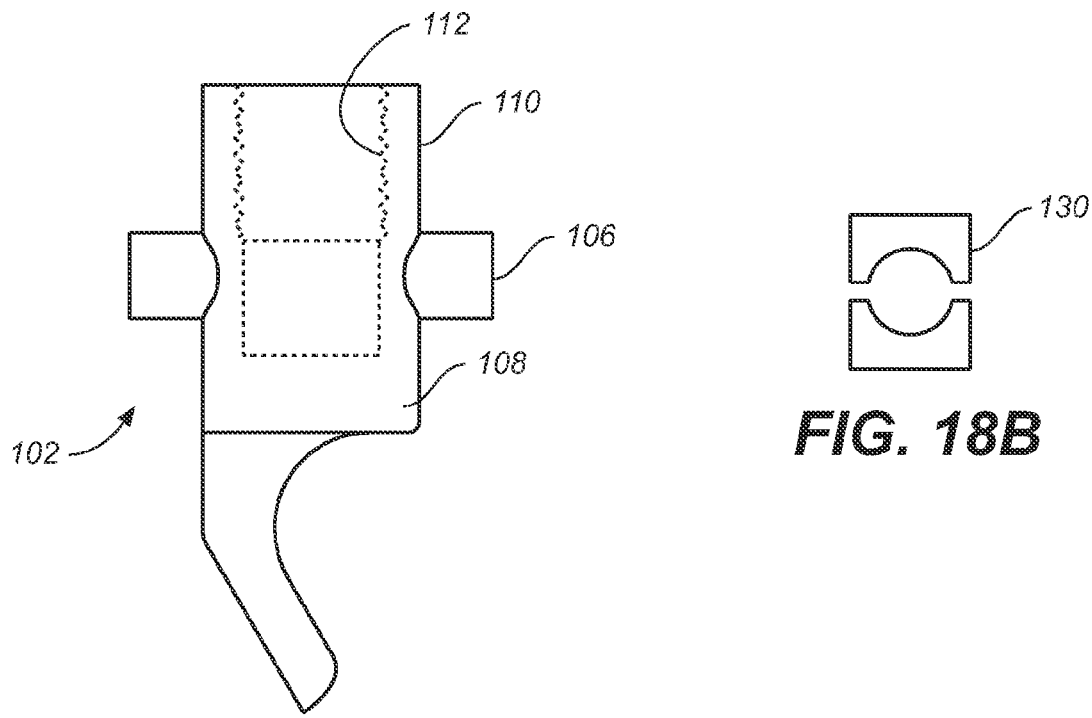
FIG. 18A
FIG. 18B
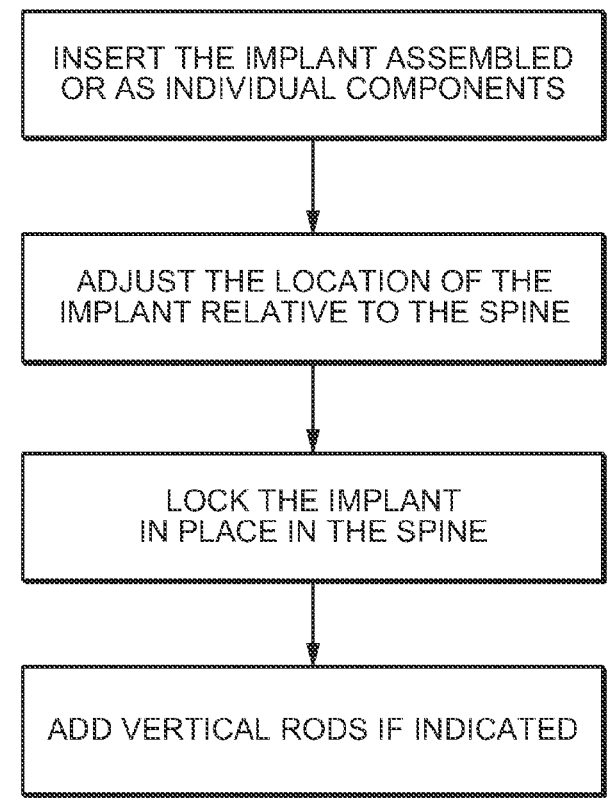
FIG. 19

IMPLANT SYSTEM AND METHOD TO TREAT DEGENERATIVE DISORDERS OF THE SPINE

CLAIM OF PRIORITY

This application claims benefit to U.S. Provisional Application No. 60/801,871, filed Jun. 14, 2006, entitled "Implant Positioned Between the Lamina to Treat Degenerative Disorders of the Spine," which is incorporated herein by reference and in its entirety.

CROSS REFERENCES TO RELATED APPLICATIONS

This application relates to, and incorporates herein by reference, each of the following in its entirety: U.S. patent application Ser. No. 11/761,006, filed Jun. 11, 2007, entitled "Implant System and Method to Treat Degenerative Disorders of the Spine,"; and U.S. patent application Ser. No. 11/761,006, filed Jun. 11, 2007, entitled "Implant System and Method to Treat Degenerative Disorders of the Spine,"

BACKGROUND OF INVENTION

The most dynamic segment of orthopedic and neurosurgical medical practice over the past decade has been spinal devices designed to fuse the spine to treat a broad range of degenerative spinal disorders. Back pain is a significant clinical problem and the annual costs to treat it, both surgically and medically, is estimated to be over $2 billion. Motion preserving devices to treat back and extremity pain have, however, created a treatment alternative to fusion for degenerative disc-disease. These devices offer the possibility of eliminating the long term clinical consequences of fusing the spine that is associated with accelerated degenerative changes at adjacent disc levels.

While total disc replacement is seen as a major advance over fusion, the procedure to implant the devices in the lumbar spine requires a major operation via an anterior approach, subjecting patients to the risk of significant complications. These include dislodgement of the device, which may damage the great vessels, and significant scarring as a consequence of the surgical procedure itself, which makes revision surgery difficult and potentially dangerous. Thus, there are advantages to spinal implants that can be inserted from a posterior approach, a technique with which spine surgeons are much more experienced. The posterior surgical approach also has the benefit of being able to directly address all pathologies that may be impinging the neural elements, which is not possible from an anterior approach. Motion preserving spinal devices that can be implanted with a minimally invasive, posterior procedure offer the benefit of less surgical trauma and faster patient recovery and also offer cost savings to payers with patients staying fewer days in the hospital.

Motion preserving devices placed posteriorly typically either rely on the spinous processes to support the implant or require pedicle screws to be inserted. However, spinous processes are not load bearing structures and are not rigid. In a population of patients with back pain, the laminae offer a much stronger structure to position an implant, since they consist of significantly stronger bone, and the laminae are also closer to the spine's axis of rotation. Pedicle screws have several disadvantages when used as attachments for motion preservation devices. The procedure to implant them is considered major surgery requiring a wide exposure. The screws are also subject to significant loads and screw loosening is a known consequence over time in these cases. Removing the screws and fusing the spine requires major revision surgery.

BRIEF DESCRIPTION OF THE DRAWINGS

FIGS. 18A, 18B are side views of another embodiment of the hook of the invention.

FIG. 19 depicts an embodiment of the method of implantation of the invention.

DETAILED DESCRIPTION OF THE PREFERRED EMBODIMENTS

In one embodiment of the present invention, an implant is provided that can be placed between the lamina through a posterior, minimally invasive surgical technique and is designed to treat degenerative disorders of the spine. Degenerative disc disease results from the natural process of aging and ultimately affects all structures of the vertebral motion segment. The degenerative process causes loads that are normally borne by the intervertebral disc to be transferred to the articular facet joints, ligaments and other soft tissues of the spine.

The benefits of this implant are: The articular facets provide an excellent structure to which to attach an implant. They consist of very strong cortical bone, the strongest in the lumbar vertebra. There are no major nerves or vessels in the area approximate to the lateral aspect of facets, making them also a very safe point of attachment.

Attached to hooks, a crosslink can be positioned as far anterior as is possible without actually impinging on the spinal canal.

The implant can be inserted through two small incisions on either side of the mid-line, preserving the spinal ligament structures, including the supraspinous ligament and the interspinous ligament and permitting the implant to placed using a minimally invasive procedure.

Figure 1:
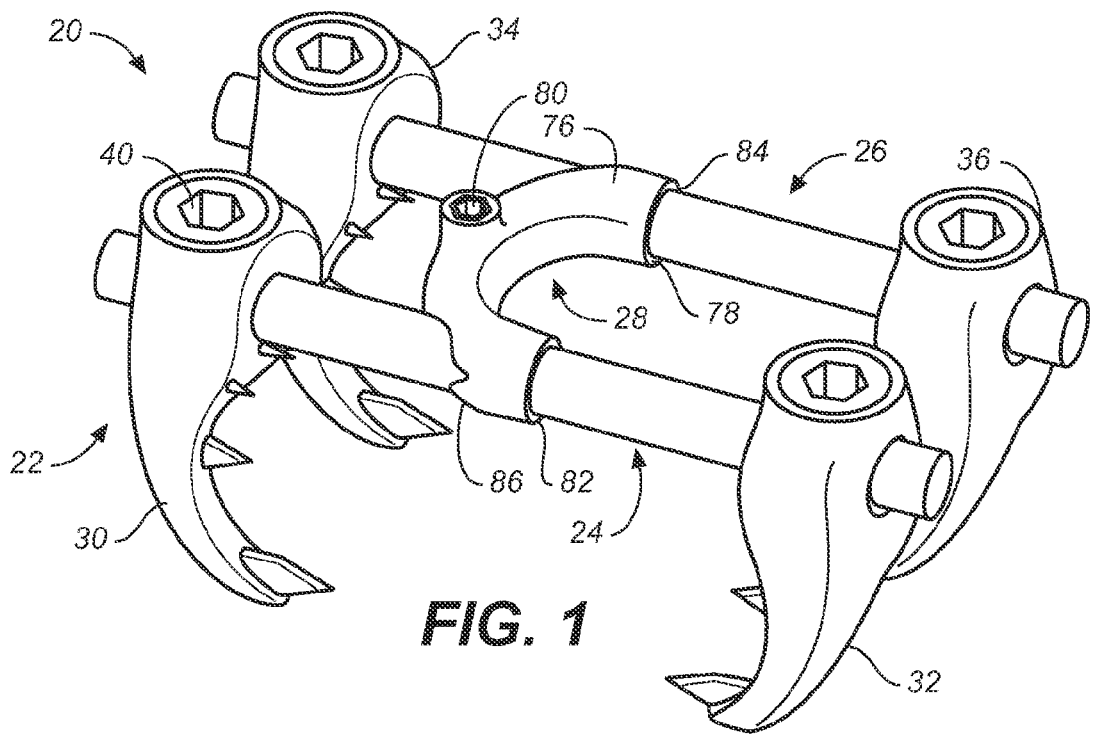
FIG. 1 is a perspective view of an embodiment of the dynamic spine stabilization, motion preservation implant of the invention.

An embodiment of the clamp implant system 20 of the invention is depicted in FIG. 1. Implant system 20 provides for dynamic stabilization and motion preservation of the spine. Implant system 20 includes anchor systems 22, horizontal rods 24, 26 and vertical connector system 28. Preferably, the anchor systems 22 and the vertical connector system 28 are made of titanium although stainless steel can also be used. The horizontal rods 24, 26 are preferably made of PEEK or other similar polymer as described below or are made of a super elastic material such as Nitinol which is an alloy of titanium and nickel. Other biocompatible materials can be used and be within the spirit and scope of the invention. Preferably, the vertical system 28 is rigid while the horizontal rods 24, 26 are flexible. Such a system 20 would accordingly have the horizontal rods made of PEEK or a similar polymer or a super elastic material while the vertical system is comprised of titanium or stainless steel. With such a system, the load that the spine places on the system would be absorbed by the horizontal rods causing the horizontal rods to flex while the vertical system remains rigid.

Figure 2:
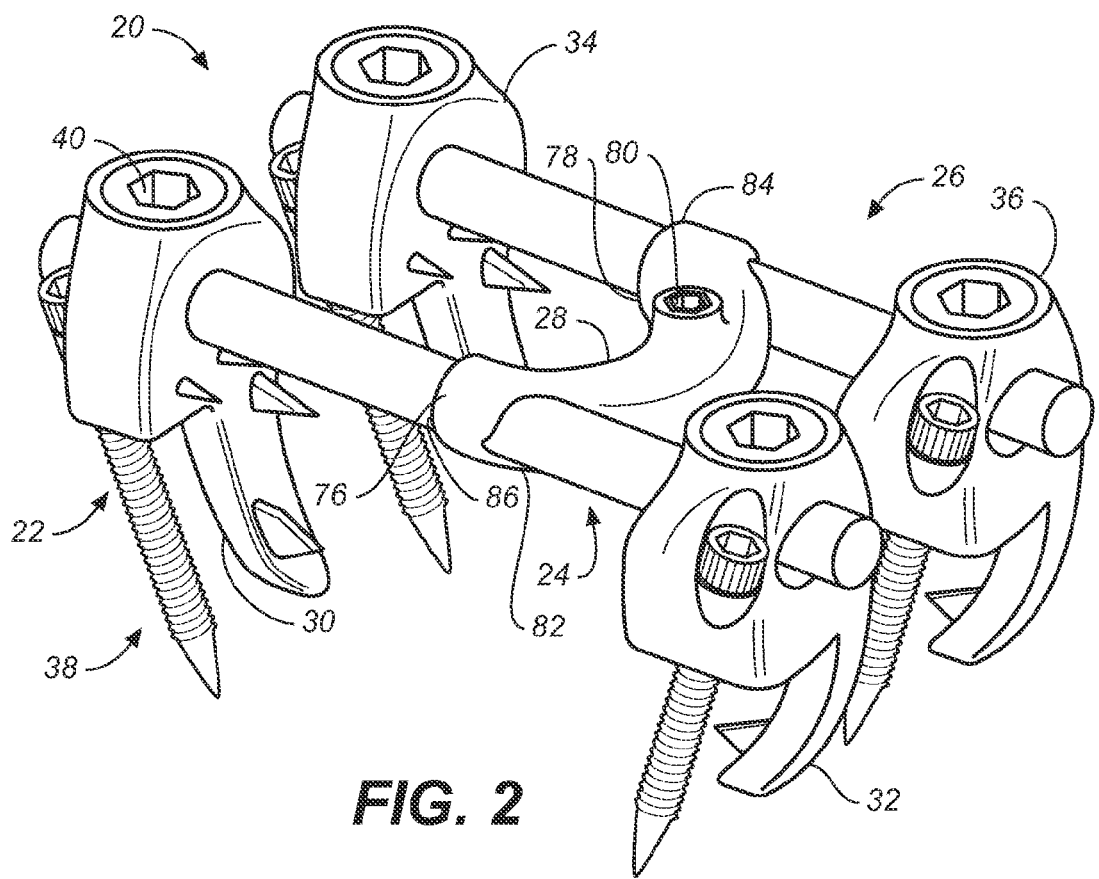
FIG. 2 is a perspective view of another embodiment of the dynamic spine stabilization, motion preservation implant with pedicle screws of the invention.

FIG. 2 includes another embodiment of the clamp implant system 20 which has an additional provision for pedicle screws 38 to assist in holding the system 20 to the spine. Elements of the embodiment of FIGS. 1, 2 that are the same have similar numerical references.

Generally, the clamping implant system 20 (FIGS. 1, 2) includes opposing clamps 30, 32 that can wrap around the facets (from posterior to anterior) and hook or angle under the facets to assist in maintaining the clamps in position and resist pull-out forces. Accordingly, the clamps 30, 32 hook or angle around the outside of the facets and are held in place by the design of the clamps 30, 32. The system 20 also includes opposing clamps 34, 36 which are the similar to opposing clamps 30, 32. The clamps 30, 32, 34, 36 have set screws 40 as explained below to lock in the horizontal rods 24, 26.

The opposing clamps 30, 32, and opposing clamps 34, 36 as can be seen in FIGS. 3, 4, 5, 6, 7, include a head 42 and a foot or hook 44. Preferably, the clamps are of one piece construction, however, as described below, the clamps can be of several piece construction with the added advantage of more degrees of freedom in implanting the clamps in the patient. The clamps 30, 32, 34, 36 include a threaded set screw bore 46 for receiving the set screw 40 and a horizontal rod bore 48 for receiving the horizontal rods 24, 26. The head 42 also includes a pedicle screw bore 50 which is preferably unthreaded and which can receive the pedicle screw 38. The bore 50 is angled in order to guide the pedicle screw into the pedicle of the spine. The head 42, accordingly, accepts in this embodiment a horizontal rod that is transversely mounted in the head and the top mounted set screw 40. As will be discussed below, the head 42 can include a split retainer, such as a split ball retainer that has a central bore for accepting the horizontal rod, and, which split retainer can be compressed by the set screw to retain the horizontal rod in the head of the clamp. The foot 44, points like a finger away from the head and in FIG. 3 looks much like an index finger of a right hand of a human extending from the rest of the hand, with the fingers and thumb of the rest of the hand folded down into the palm of the human hand. Stated another way there is an L-shaped junction between the head 42 and the foot or hook 44. As is evident from the figures, there is in this preferred embodiment, a continuous transition from the head 42 to the foot or hook 44. The inner surface of the foot 44 can be comprised of a textured surface to provide for bony ingrowth of the spine bone into the foot 44. Also the inner surface can be coated with bone growth inducing materials such as bone morphogenetic proteins or BMPs. The inner surface of the foot 44 in this preferred embodiment, is comprised of a compound surface that can accommodate the anatomical shape of the facets in order to secure the clamps about the facets. In this embodiment, the foot 44 has a first radius of curvature 52 (FIG. 5) which defines the first curve of the foot along the length of the foot. The foot 44 also includes a second radius of curvature 54 (FIG. 6) which defines the second curve of the foot across the width of the foot with the first curve and the second curve in this embodiment being about perpendicular to each other. The first curve runs about vertically and the second curve runs about horizontally. In this embodiment the first radius of curvature is about 0.625 inches and the second radius of curvature is about 0.785 inches. These curves allow the foot or hook 44 to optimally conform to the anatomical shape of the outside of the facet with a contour for maximum contact area. In this preferred embodiment, the clamps 30, 32, 34, 36 have about up to 40 degrees of adjustment upon implantation relative to the coronal orientation of the spine and up to about 10 degrees of adjustment upon implantation relative to the sagittal orientation of the spine.

Figure 3:
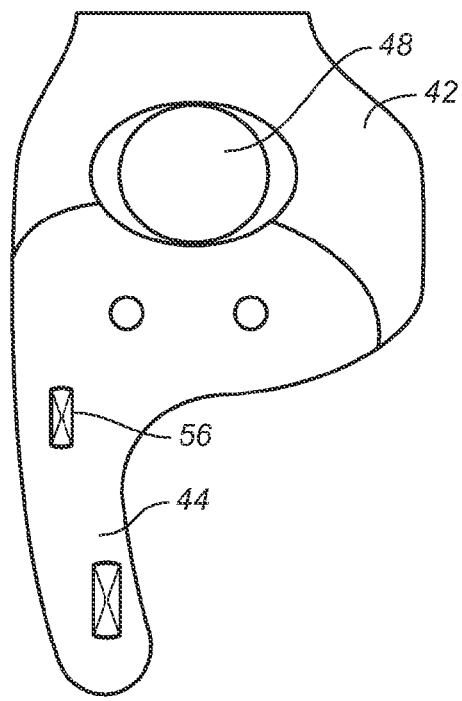
FIG. 3 is a side view of an embodiment of a hook of the invention of the embodiment of FIG. 2.
Figure 5:
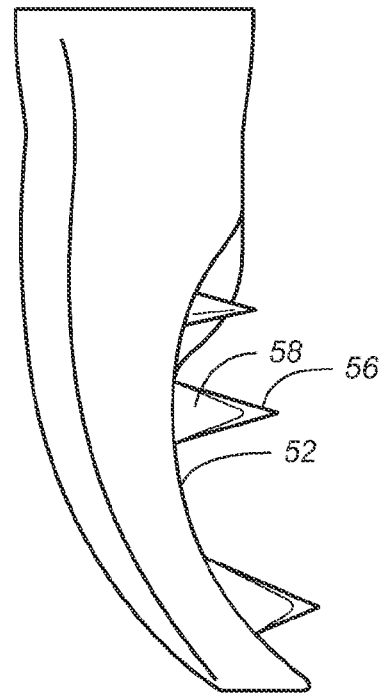
FIG. 5 is an end view of the embodiment of the hook of the embodiment of the invention of FIG. 3.
Figure 4:
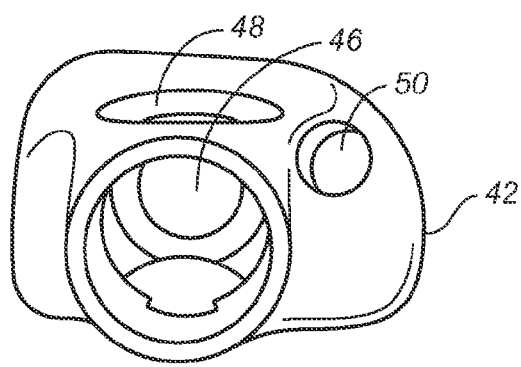
FIG. 4 is a top view of the embodiment of the hook of the embodiment of the invention of FIG. 3.
Figure 6:
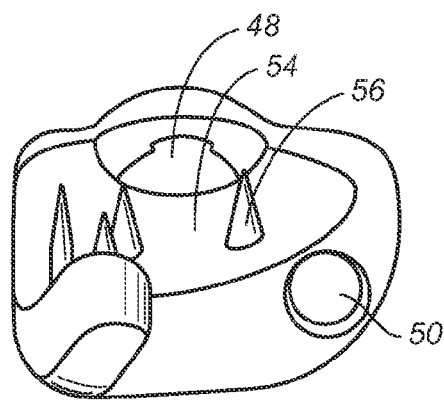
FIG. 6 is a bottom view of the embodiment of the hook of the embodiment of the invention of FIG. 3.

As can be seen in FIGS. 3, 5, 6, spikes 56 extend from the inner surface of the foot or hook 44 of the clamps 30, 32, 34, 36. These spikes 56 are used to also secure the foot or hook 44 to the outer surface of the facets. The tips of the spikes 56 are designed to cut and penetrate the facet bone and not to compress the facet bone. The spikes have flat surfaces 58 that increase lateral resistance to lateral movement of the clamps 30, 32, 34, 36, and, thus, assist in preventing the clamps from working themselves out of engagement with the facets. The spines 58 are arranged down the length of the foot 44 and across the base of the foot 44, where the foot 44 transitions to the head 42. As depicted, the spikes 56 are arrayed in the foot in order to obtain optimal stability of the clamp as secured to the facets. The smooth transition between the head 42 and the foot 44 allows for, in this embodiment, continuous sagittal adjustment. This additionally allows for optimal positioning and orientation of the horizontal rods 24, 26 upon implantation of the system 20. The shape and radii of the foot and the transition from the head to the foot allow the clamp to match the anatomical variations in the junction between the transverse process and articular processes of the spine.

Figures 7, 9:
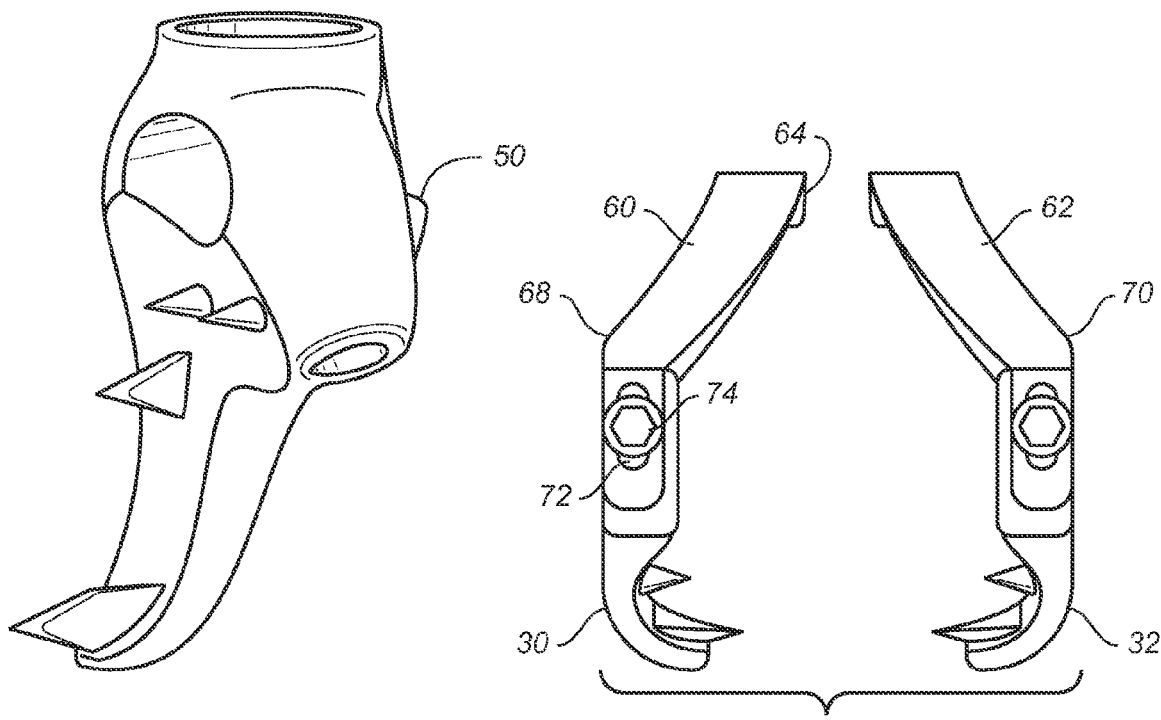
FIG. 7 is a side perspective view of the embodiment of the hook of the embodiment of the invention of FIG. 3.
FIG. 9 is a top view of the embodiment of the invention of FIG. 8.
Figure 8:
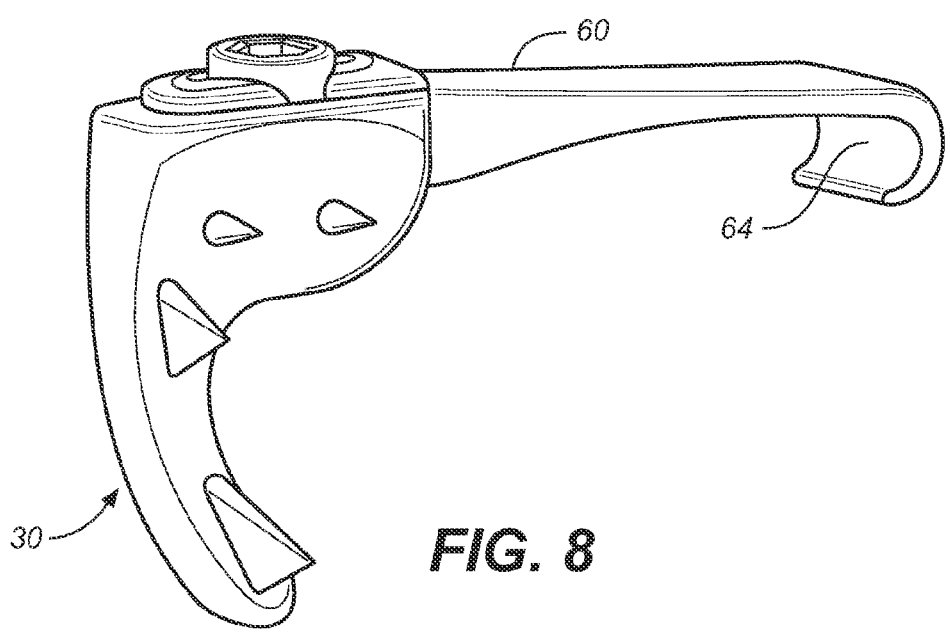
FIG. 8 is a side perspective view of another embodiment of the hook of the invention.
Figure 10:
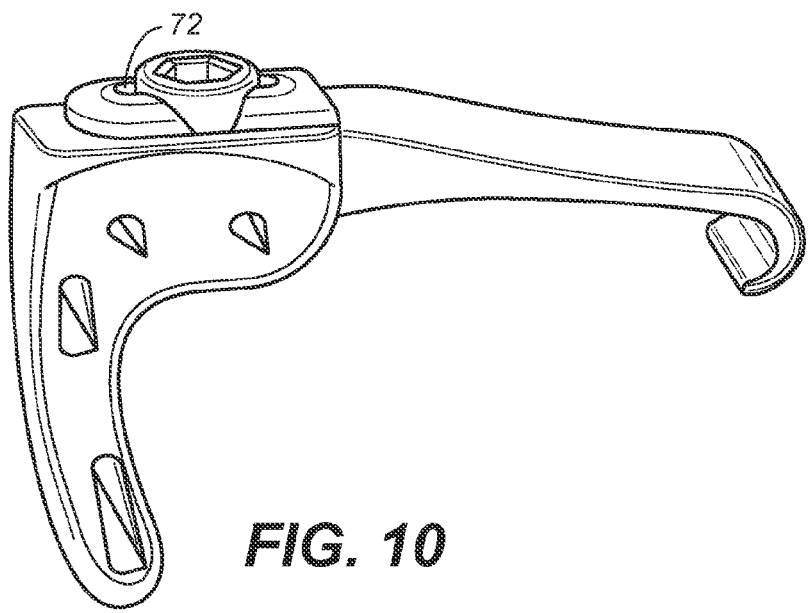
FIG. 10 is a side view of the embodiment of the invention of FIG. 8.

FIGS. 8, 9, 10, depict alternative embodiments of the clamps 30, 32, 34, 36, which have lamina articular process hooks 60, 62 which have a hook element 64, 66, respectively, that is curved to fit around the lamina and assist in holding the clamp in place in the spine. The hooks 60, 62 include adjustable arms 68, 70 that can adjust to the size of the lamina of the spine. As is evident from FIGS. 8, 9, 10, each arm 68, 70 includes an elongate slot such as slot 72 with a set screw such as set screw 74, provided through said slot 72. The set screw 74 is mounted in a threaded bore in the clamp 30 and the arm 68 can slide relative to the rest of the clamp to adjust to the spine and then the arm 68 can be locked into position by the set screw. It is evident from the depiction that clamp 30 in FIGS. 8, 9, 10, has a different head than the head depicted in the prior embodiment of the clamp 30. In order to accommodate the laminar hooks 60, 62, the embodiments of the clamp 30 in FIGS. 1-7 can be modified in a number of ways. For example, the top of the head of the clamp in these figures can be widened to accept the arm 68 and the set screw 74, and, thus, both the set screw 40 and the set screw 74, can be tightened from the top of the head of the clamp. Alternatively, the slot 72 of the arm can be rotated by about ninety degrees so that the set screw can lock the arm to the clamp along the outside of the clamp, opposite to the surface of the clamp that has the spines and conforms to the surface of the facet. It is also to be understood that the clamps 30, as they appear in FIGS. 8, 9, 10, can be used by themselves to repair fractures of the pars interarticularis on the lamina of the spine.

The horizontal rods 24, 26 can have variable lengths and diameters in order accommodate the shape of the spine. Preferably, the diameters of the horizontal rods 24, 26 can be selected to adjust the dynamic stabilization, motion preservation feature afforded by these embodiments. Larger diameter, generally, will provide for a stiffer system while smaller diameters will provide for a less stiff system. For the same diameter, rods made of PEEK will provide for a stiffer system than rods made of a super elastic material. Also rods made of stainless steel will be stiffer than rods made of titanium. PEEK rods will be less stiff than rods made of titanium or stainless steel. Accordingly, the rods can be selected to give the degree of flex desired, and, thus, the degree of dynamic stabilization desired in response to dynamic loads placed on the system 20 by the spine in motion. It is to be understood that the horizontal rods can also be bent or bowed out in order to accommodate the anatomical structures of the spine.

The vertical connector system 28 in FIGS. 1, 2, connect adjacent horizontal rods 24, 26, which horizontal rods are associated with different vertebral levels. In this embodiment the vertical connector system 28 is about U-shaped. The vertical connector system 28 includes an upper half connector 76 joined to a lower half connector 78, along the split line 86, by a locking screw 80. With the upper connector and the lower connector joined, the system 28 defines a first horizontal rod capture bore 82 and a second horizontal rod capture bore 84. The vertical connector systems 28 are curved at the midpoint or apex of the curve in order to accommodate, and, thus, preserve the spinous processes and the associated ligaments. In this particular embodiment, the locking screw 80 is located at the midpoint and is used to lock the system 28 about the first and second horizontal rods 24, 26. It is to be appreciated that another vertical connector system 28 can be used with the system 20 in order to impart additional stiffness. If two systems 28 were used, one would be closer to the first clamp 30 (also clamp 34) and the other would be closer to the second clamp 32 (also clamp 36) in order to accommodate the spinous processes and ligament structures of the spine. If two systems 28 were used, the set screws 80 and the midpoint or apex of each system would be closer to the respective clamps in order to define a large opening between the two vertical connector systems 20 to accommodate the spinous processes and associated ligaments. If desired, the vertical connector system can be made of a less stiff biocompatible material as discussed herein, should additional flexibility be desired.

Figure 11:
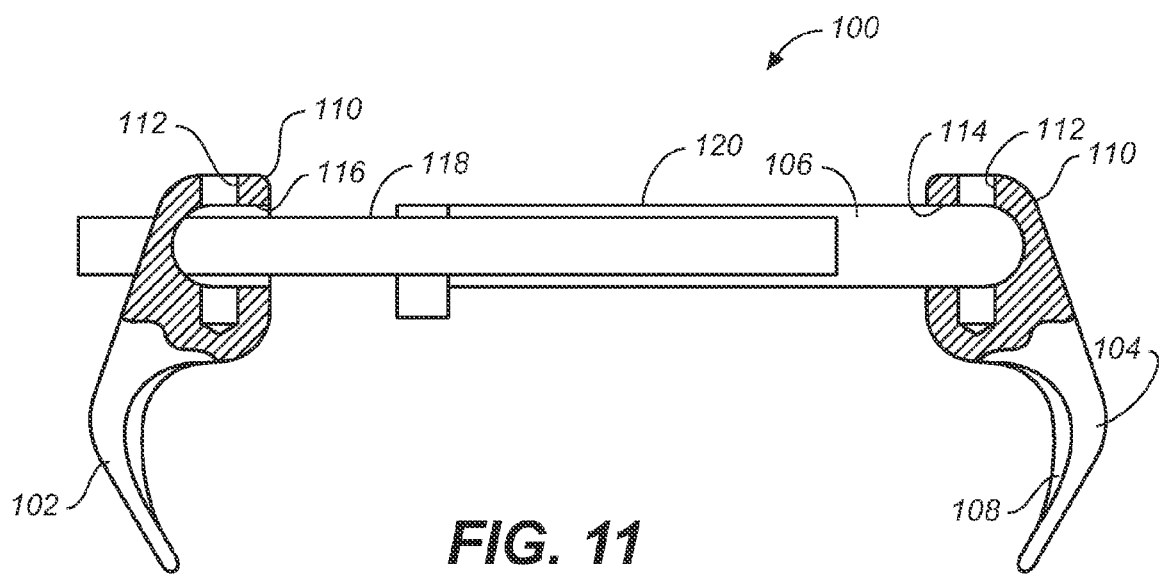
FIG. 11 is a side partially sectioned view of another embodiment of an implant of the invention.
Figure 12:
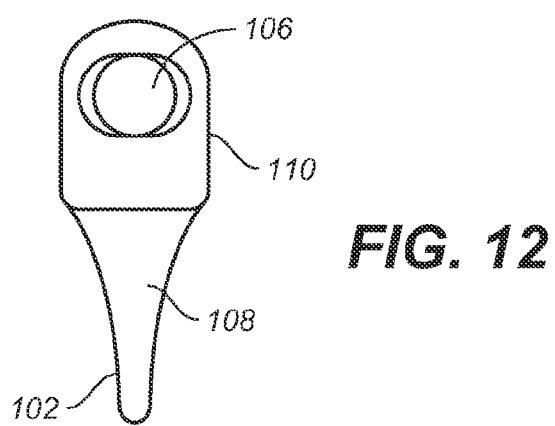
FIG. 12 is a side view of an embodiment of a hook of the embodiment of the invention of FIG. 11.
Figure 13:
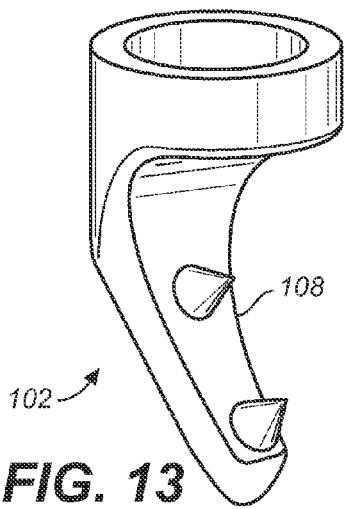
FIG. 13 is a perspective view of a hook with barbs of an embodiment of the invention to be used with the embodiment of the invention of FIG. 11.
Figure 14:
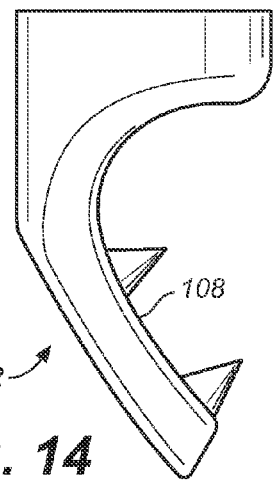
FIG. 14 is a side view of the embodiment of the hook of the invention of FIG. 13.

Referring to FIGS. 11, 12, another embodiment of the present invention is an implant, generally denoted as 100, with a first hook 102, a second hook 104 and a cross-link or horizontal rod 106 coupled to the first and second hooks 102 and 104. The first and second hooks 102 and 104 have geometries that conform to a lateral border of a superior articular facet.

In various embodiments, the implant (i) engages the laminae to stabilize the spine in a dynamic manner, and (ii) can be made stiff enough to rigidly stabilize the spine as an aid to a fusion.

In one embodiment, the first and second hooks have radii to provide conformance with the spine. As discussed below, the first and second hooks 102 and 104 can be symmetrical in a sagittal orientation and free to rotate around a coronal axis. The first and second hooks 102 and 104, can provide an ability to adjust to, and be affixed to, the articular facets. In one embodiment, the first and second hooks 102 and 104 include at least one member to engage with the articular facet. This member can be a fin, stud, spike, and the like, as discussed above with respect to other embodiments.

Further as seen in FIGS. 11, 12, the hooks include a ventral or lower hooked section 108 and an dorsal or upper head section 110. The hooked section 108 can conform to the spine as described herein and the head section 110 can mount the cross-link or horizontal rod 106. The head sections 110 can include a top bore 112 that is threaded and can accept a set screw to lock the horizontal rod 106 in place. The head section 110 also includes either (1) a recess 114 that can receive an end of the horizontal rod 106 such that the set screw can lock the rod 106 in place, or (2) a bore 116 through which the rod 106 can be received so that the spacing between the hooks 102, 104 can be adjusted. Once the rod 106 is received in the bore 116 and the spacing of the hooks 102, 104 is adjusted by sliding the hook 102 on the rod 106, a set screw can be used to lock the rod 106 in place. It is to be understood, that procedurally and preferably, the hooks 102, 104 are placed adjacent to the facets and the length between the hooks is adjusted prior to the tightening of the set screws to lock the rod 106 and the hooks 102, 106 together. Alternatively, the rod 106 can be telescoping such that a first portion 118 of the rod 106 can slide into a second portion 120 of the rod 106 in order to adjust the length of the rod 106. If desired, an additional set screw can be mounted on the second portion 120 of the rod 106 to lock the first portion to the second portion of the rod.

As illustrated in FIGS. 13, 14, 15, 16, 17A, 17B the first and second hooks such as hook 102 can have a ventral or lower section 108 and dorsal or upper sections 110 that can move and in this embodiment, rotate relative to each other. The ventral or lower hooked sections 108 has a freedom of motion about an axial plane to allow for variations in anatomy of the articular facet. The dorsal or upper section 110 accepts the horizontal rod 106. The dorsal or upper section 110, as previously discussed, includes a recess or bore to accept the horizontal rod 106. In this embodiment, the horizontal rod 106 rests in the saddle or head or upper portion 110 and a set screw locks the horizontal rod in place in the head.

Figure 15:
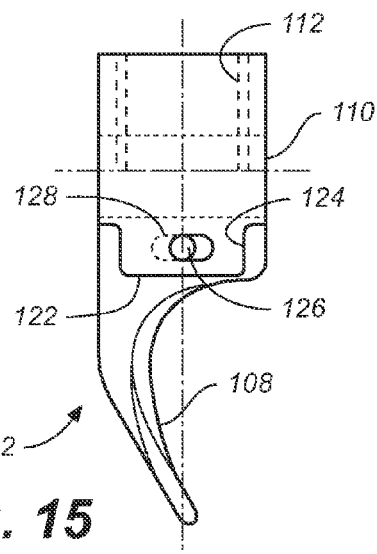
FIG. 15 is a side view of another embodiment of the hook of the invention.
Figure 16:
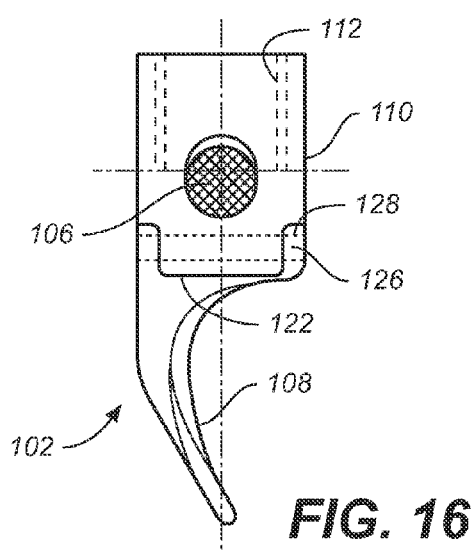
FIG. 16 is a side view of the another embodiment of the hook of the invention of FIG. 15 in a different orientation.
Figure 17A:
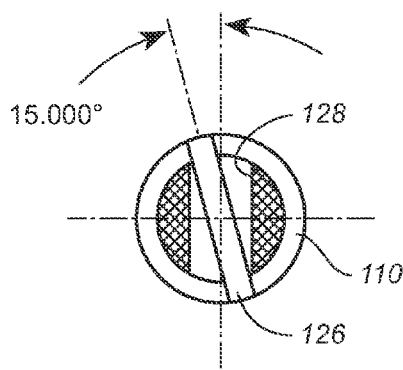
FIGS. 17A, 17B are schematical top views of the embodiment of FIG. 15.
Figure 17B:
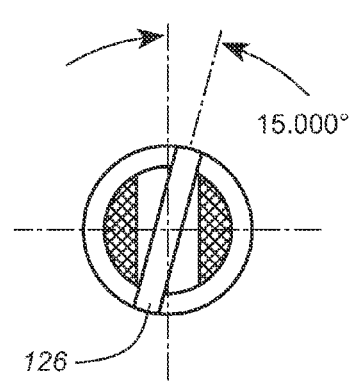

As depicted in FIGS. 15, 16, 17A, 17B, the lower hooked portion 108 can rotate relative to the upper head portion 110. The rotation occurs at split line 122. Preferably, the upper portion 110 can snap into the lower portion 108 and be captured under a lip of the cylindrical recess of the lower portion 108. Thus, the upper portion 110 can rotate in the recess 122 of the lower portion 108 at the split line 122. If desired the rotation can be limited by a limit rod 126 that is mounted on the lower portion 108 and projects through the cylindrical recess 122. The upper portion includes an enlarged bore 128 through which the limit rod 126 is received, when the upper portion is assembled with the lower portion of the hook 102. In a preferred embodiment, the limit rod allows the upper portion of the hook 102 to rotate about 15 degrees on each side of a central axis, for a total of about 30 degrees of rotation. It is to be understood that 360 degrees of rotation is possible with the limit rod 126 removed, and also that changes to the size of the bore 128 can be made to adjust the degree of rotation of the upper portion to the lower portion or the hook 102. Accordingly, the first and second hooks 102 and 104 illustrated in FIGS. 15, 16 are adjustable and can be re-adjusted after the hooks 102 and 104 are initially implanted.

In the embodiment of FIGS. 18A, 18B, the horizontal rod 106 is configured to be fixed with compression applied by a set screw received though bore 112 in head 1110. The set screw can fix an orientation of the ventral or upper section 108 of the hooks 102 and horizontal rod 106, as well as, lock the upper portion of the hook to the lower portion 108 at the same time. In this embodiment, the horizontal rod 106 can be received in a compression block 130 that is received in the bore 112. Generally, the compression block is cylindrical and can be comprised of two pieces which mate with facing recesses that can receive the horizontal rod 106. Alternatively, the compression block can be a one piece construction with a slit. In either embodiment, the set screw, when turned down in the bore 112, causes the compression block 130 to compress about, and without causing damage to, the horizontal rod 106 to lock the rod in place.

In one embodiment, the horizontal rod 106 has a flat surface that conforms to a laminar anatomy or a contoured surface to match the laminar anatomy.

In another embodiment of the present invention, the implant 100 includes an artificial ligament attached to the horizontal rod 106. The artificial ligament can be looped around the superior spinous process and then re-attached to the horizontal rod 106. The artificial ligament provides a limit to flexion and increases rigidity of the implant. The artificial ligament can be made of a biocompatible material.

In another embodiment of the present invention, an implant assembly is provided that has first and second implants 100. The first and second implants 100 can be coupled by at least one vertically running rod configured to provide rigid stability as an aid in fusing the spine.

It is to be understood that the various features, designs and functions of the various embodiments can be selected for and or combined in other embodiments as is advantageous.

With respect to the method of implantation (FIG. 19), the hooks can be placed adjacent to the facets, and then the position of the horizontal rod relative to the hooks can be adjusted. The hooks can be pressed into the bone and the set screws can be tightened to hold the hooks and horizontal rod in place. With two such configurations in the spine, the configurations can be connected with vertical rods and the like. Alternatively, the implant, including the hooks and the horizontal rod loosely coupled together, can be inserted as an assembly and then once positioned, the set screws can be tightened to lock the system 100 in place in the spine.

Materials for use with the implant include the following:

As indicated above, the implant can be made of titanium, stainless steel, super elastic materials and/or polymers such as PEEK.

In addition to Nitinol or nickel-titanium (NiTi) other super elastic materials include copper-zinc-aluminum and copper-aluminum-nickel. However for biocompatibility the nickel-titanium is the preferred material.

Other suitable material include, by way of example, only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

Preferably, the horizontal rods are made of PEEK or a similar polymer or a super elastic material, which materials are flexible, or the rods are made of another flexible material, and the anchors and the vertical systems are made of titanium or stainless steel which are stiff or made of another stiff material.

Further, it should be apparent to those skilled in the art that various changes in form and details of the invention as shown and described may be made. It is intended that such changes be included within the spirit and scope of the claims appended hereto. The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. An implant comprising:
a first bone anchor including,
  a first head and a first tip, and
  a first engaging surface adapted to engage a first lateral surface of a vertebra, the first engaging surface being continuously curved with a first radius of curvature along a first longitudinal axis between the first head and the first tip and being continuously curved with a second radius of curvature larger than the first radius of curvature perpendicular to said first longitudinal axis;
a second bone anchor including,
  a second head and a second tip, and
  a second engaging surface adapted to engage a second lateral surface of the same vertebra opposite the first lateral surface,
  the second engaging surface being continuously curved with said first radius of curvature along a second longitudinal axis between the second head and the second tip and being continuously curved with said second radius of curvature perpendicular to said second longitudinal axis;
a flexible horizontal rod connected to the first head of the first bone anchor and the second head of the second bone anchor;
wherein the first head of the first bone anchor and the second head of the second bone anchor are spaced apart along the flexible horizontal rod by an adjustable distance;
wherein the adjustable distance can be reduced in order to cause the first engaging surface of the first bone anchor to engage the first lateral surface of a vertebra and cause the second engaging surface of the second bone anchor to engage the second lateral surface of the same vertebra and thereby secure the flexible horizontal rod to the vertebra; and
a third bone anchor adapted to be attached to a first portion of another vertebra;
a fourth bone anchor adapted to be attached to a second portion of the same another vertebra;
another flexible horizontal rod connected to the third bone anchor and the fourth bone anchor; and a rigid vertical rod;
the rigid vertical rod connected between the flexible horizontal rod and the another flexible horizontal rod;
wherein the rigid vertical rod is connected to the flexible horizontal rod at a position about halfway between the first bone anchor and the second bone anchor and spaced from the first bone anchor and the second bone anchor; and
wherein the rigid vertical rod is connected to the another flexible horizontal rod at a position about halfway between the third bone anchor and the second bone anchor and spaced from the third bone anchor and the fourth bone anchor.

2. The implant of claim 1 wherein at least one of the flexible horizontal rods is meant to absorb and be deflected with respect to at least in part the motion of the spine.

3. The implant of claim 1 wherein said rigid vertical rod is curved so as to be adapted to avoid a spinous process of a spine which is located between the flexible horizontal rod and the another flexible horizontal rod.

4. The implant of claim 1, wherein:
said first radius of curvature is about 0.625 inches; and
said second radius of curvature is about 0.785 inches.

5. An implant comprising:
a first clamp having,
    a first head and a first tip, and
    a first engaging surface adapted to engage a first lateral surface of a vertebra,
    the first engaging surface being continuously curved with a first radius of curvature along a first longitudinal axis between the first head and the first tip and being continuously curved with a second radius of curvature larger than the first radius of curvature perpendicular to said first longitudinal axis;
a second clamp having,
    a second head and a second tip, and
    a second engaging surface adapted to engage a second lateral surface of the same vertebra opposite the first lateral surface,
    the second engaging surface being continuously curved with said first radius of curvature along a second longitudinal axis between the second head and the second tip and being continuously curved with said second radius of curvature perpendicular to said second longitudinal axis;
a flexible horizontal rod connected through the first head of the first clamp and connected through the second head of the second clamp;
wherein the first head of the first clamp and the second head of the second clamp are spaced apart along the flexible horizontal rod by an adjustable distance;
wherein the adjustable distance can be reduced in order to cause the first engaging surface of the first clamp to engage the first lateral surface of a vertebra and cause the second engaging surface of the second clamp to engage the second lateral surface of the same vertebra and thereby secure the flexible horizontal rod to the vertebra; and
wherein the flexible horizontal rod is configured for attachment of a spinal rod at a position between the first head and the second head, and the flexible horizontal rod is adapted to flex in response to a load placed on the flexible horizontal rod by the spinal rod such that the spinal rod can move relative to the first clamp and the second clamp.

6. The implant of claim 5 including at least a first lock configured to fix the adjustable distance between the first head of the first clamp and the second head of the second clamp and thereby secure the flexible horizontal rod to the vertebra.

7. The implant of claim 5 wherein said first engaging surface extends from said first head substantially perpendicular to said flexible horizontal rod.

8. The implant of claim 5 including a first lock to lock the first head of the first clamp to the flexible horizontal rod and a second lock to lock the second head of the second clamp to the flexible horizontal rod and wherein the locking of the first and second heads to the flexible horizontal rod with the first and second clamps positioned relative to one vertebra locks the adjustable distance between first head of the first clamp and the second head of the second clamp and secures the implant to the one vertebra.

9. The implant of claim 5, wherein:
the first engaging surface is configured and adapted to engage a first articular facet of a vertebra; and
the second engaging surface is configured and adapted to engage a second articular facet of the same vertebra opposite the first articular facet.

10. The implant of claim 5, wherein:
the first engaging surface is concave; and
the second engaging surface is concave.

11. The implant of claim 5, wherein:
said first radius of curvature is about 0.625 inches.

12. The implant of claim 5, wherein:
the first engaging surface comprises a plurality of spikes adapted to cut and penetrate bone; and
the second engaging surface comprises a plurality of spikes adapted to cut and penetrate bone.

13. The implant of claim 5, wherein:
said first radius of curvature is about 0.625 inches; and
said second radius of curvature is about 0.785 inches.

14. An implant comprising:
a flexible horizontal rod having a first end and a second end;
a first clamp mounted adjacent the first end of the flexible horizontal rod;
said first clamp including a first engaging surface extending along a first longitudinal axis away from said flexible horizontal rod and adapted and configured to engage a first lateral surface of the vertebra;
the first engaging surface being continuously curved with a first radius of curvature along said first longitudinal axis and being continuously curved with a second radius of curvature larger than the first radius of curvature perpendicular to said first longitudinal axis;
a second clamp mounted adjacent the second end of the flexible horizontal rod;
said second clamp including a second engaging surface extending along a second longitudinal axis away from said flexible horizontal rod and adapted and configured to engage a second lateral surface of the vertebra opposite the first lateral surface;
the second engaging surface being continuously curved with said first radius of curvature along said second longitudinal axis and being continuously curved with said second radius of curvature perpendicular to said second longitudinal axis;
wherein the first clamp is separated from the second clamp by a first distance; and
wherein the first distance is adjustable such that, by reducing the first distance, the first engaging surface of the first clamp and the second engaging surface of the second clamp can be brought into engagement with opposite lateral sides of a vertebra in order to secure the flexible horizontal rod to the vertebra.

15. The implant of claim 14 wherein said first engaging surface is curved and said second engaging surface is curved.

16. The implant of claim 15 wherein said first engaging surface is concave and said second engaging surface is concave.

17. The implant of claim 14, wherein:
said first engaging surface comprises a plurality of spikes adapted to cut and penetrate bone; and
said second engaging surface comprises a plurality of spikes adapted to cut and penetrate bone.

18. The implant of claim 14, wherein:
said first radius of curvature is about 0.625 inches; and
said second radius of curvature is about 0.785 inches.

19. The implant of claim 14, comprising at least one lock configured to fix the first distance between the first clamp and the second clamp and thereby secure the first flexible horizontal rod to the first vertebra.

20. The implant of claim 14, further comprising:
a rigid spinal rod connected to the flexible horizontal rod at a position about halfway between the first clamp and the second clamp and spaced from the first clamp and the second clamp;
wherein said rigid spinal rod is configured and adapted to support a load from an adjacent vertebra; and
wherein the flexible horizontal rod is adapted to flex in response to a load placed on the flexible horizontal rod by the rigid spinal rod such that the rigid spinal rod can move relative to the first clamp and the second clamp.

* * * * *